United States Patent [19]
Marsh et al.

[11] Patent Number: 6,071,737
[45] Date of Patent: Jun. 6, 2000

[54] EQUINE NEOSPORA ISOLATE AND ITS USES

[75] Inventors: Antoinette E. Marsh, Columbia, Mo.; Patricia A. Conrad; Bradd C. Barr, both of Davis, Calif.

[73] Assignee: The Regents of the University of California, Oakland, Calif.

[21] Appl. No.: 09/042,600

[22] Filed: Mar. 16, 1998

[51] Int. Cl.$^7$ .................................................. C12N 1/14
[52] U.S. Cl. ........................................................ 435/258.1
[58] Field of Search .......................................... 435/258.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,902,505 | 2/1990 | Pardridge et al. | 424/85.7 |

OTHER PUBLICATIONS

Edward S. Reynolds, "The use of lead citrate at high pH as an electron–opaque stain in electron microscopy," *J. Cell. Biol.* 17:208–212 (1963).

Norman D. Levine, Ph.D., *Veterinary Protozoology*, Iowa State University Press, Ames. pp. 13–15 (1985).

Dubey, et al., "Newly recognized fatal protozoan disease of dogs," *J. Am. Vet. Med. Ass'n.* 192(9) :1269–1270 (May 1, 1988).

Bjerkas, et al., "Immuno–histochemical and ultrastructural characteristics of a cyst–forming sporozoon associated with encephalomyelitis and myositis in dogs," *Acta. Path. Microbiol. Immunol. Scandinavica* 96:445–454 (1988).

Dubey, et al., "Neonatal *Neospora caninum* infection in dogs: isolation of the causative agent and experimental transmission," *J. Am. Vet. Ass'n.* 193 (10) :1259–1263 (Nov. 15, 1988).

Speer, et al., Ultrastructure of tachyzoites, bradysoites and tissue cysts of *Neospora caninum*, *J. Protozool.* 36(5) : 458–463 (1989).

Dobeli, et al., "Expression, purification, biochemical characterization and inhibition of recombinant *Plasmodium falciparum* aldolase," *Mol. and Biochem. Parasit.* 41:259–268 (1990).

Anderson, et al., "Neospora–like protozoan infection as a major cause of abortion in California dairy cattle," *J. Am. Vet. Med. Ass'n.* 198(2) :241–244 Jan. 15, 1991.

Barr, et al., "Neospora–like protozoal infections associated with bovine abortions," *Vet. Pathol.* 28:110–116 (1991).

Barr, et al., "Neospora–like encephalomyelitis in a calf: pathology, ultrastructure, and immunoreactivity," *J. Vet. Diagn. Invest.* 3:36–46 (1991).

Tice, et al., "Parenteral drug delivery: injectables," *Treatise on Controlled Drug Delivery*, A. Kydonieus, ed., Marcel Dekker, Inc., New York, NY, pp. 315–339 (1992).

Barr, et al., "Neospora–like protozoal infections asociated with abortion in goats," *J. Vet. Diagn. Invest.* 4:365–367 (1992).

Dubey, et al., "*Neospora caninum* (Apicomplexa) in a stillborn goat," *J. Parasitol* 78(3) :532–534 (1992).

J. P. Dubey, "A review of *Neospora caninum* and Neospora–like infections in animals," *J. Protozool. Res.* 2:40–52 (1992).

Lindsay, et al., "Use of infected cultured cells to compare ultrastructural features of *Neospora caninum* from dogs and *Toxoplasma gondii*," *Am. J. Vet. Res.* 54(1) :103–106 (Jan. 1993).

Conrad, et al., "In vitro isolation and characterization of a Neospora sp. from aborted bovine foetuses," *Parasitology* 106:239–249 (1993).

Barr, et al., "Experimental fetal and transplacental Neospora infection in the nonhuman primate," *Lab. Invest.* 71(2) :236–242 (1994).

Woods, et al., Systemic Neosporosis in a California black–tailed deer (*Odocoileus hemionus columbianus*) , *J. Vet. Diag. Invest.* 6:508–510 (1994).

Marsh, et al., "Sequence analysis and comparison of ribosomal DNA from bovine Neospora to similar coccidial parasites," *J. Parasitol.* 81(4) : 530–535 (1995).

Gray, et al., "Visceral neosporosis in a 10–year–old horse," *J. Vet. Diagn. Invest.* 8:130–133 (1996).

Marsh, et al., Neosporosis as a cause of equine protozoal myeloencephalitis, *J. Am. Vet. Med. Ass'n.* 209 (11) : 1907–1913 (Dec. 1, 1996).

Daft, et al., "Case reports. *Neospora encephalomyelitis* and polyradiculoneuritis in an aged mare with Cushing's disease," *Equine vet. J.* 28 (3) :240–243 (1996).

Yamane, et al., "In vitro isolatin and characterisation of a bovine Neospora species in Japan," *Res. Vet. Sci.* 63:77–80 (1997).

Stenlund, et al., Characterization of a Swedish bovine isolate of *Neospora caninum*, *Parasitology Res.* 83:214–219 (1997).

*Primary Examiner*—Donna C. Wortman
*Attorney, Agent, or Firm*—Townsend & Townsend & Crew LLP

[57] ABSTRACT

The present invention provides isolated equine Neospora cultures. The cultures are used to develop diagnostic assays for the detection of Neospora infections in horses and other animals. Also provided are pharmaceutical compositions for the treatment and prevention of Neospora infections.

2 Claims, 2 Drawing Sheets

MARSH, A.E. ET AL.

NEOSPORA EQUI (EQUINE NEOSPORA ISOLATE)
INTERNAL TRANSCRIBED SPACER 1 REGION OF rRNA GENE
EN 1 ITS 1 SEQUENCE

ACACGRCCTT TATTCTTTTC AACCCTCAAC CTTTGAATCC CAAGCAAAAC
ATGAGCTTGT ATCCCTCTCC TTTGGAGAGG GGTACATTCA AGAAGAGTGA
TATACTACTC CCTGTGAGTT GTATCGCCTT CTTCATGTGG ATATTTTGCA
CTACTTTTTT CAAGCGTTCT ATTGAACGCC TGATAATGAA AGTGTGTGCA    (SEQ ID NO. 1)
TATATCCGGG AGTGTACGGC GAAGGGACTC GGTCACTGGA AATTAACGTC
TCTATTGGGA CTTTAACTTC CAGGAGTTTC TTCAATGTGC ATTCTTTTTT
CCCACACCGT TATTTAAAC AACAAATCTG GATAGCGTTT GATGGAAGAG
AAAGATGGTC TCTTTCTGTA TTTCTCTCTA TTCGCTTTCA GATTACCTAC
TAAAAACTAT AATGTTTTTC TAAATTTTCA GCAATGGA

NEOSPORA CANINUM (CN1 AND BPA1 DNA SEQUENCE)
INTERNAL TRANSCRIBED SPACER 1 REGION OF rRNA GENE
BPA1 ITS 1 SEQUENCE

ACACGTCCTT TATTCTTTTC AACCCTCAAC CTTTGAATCC CAAACAAAAC
ATGAGCTTGT ATCCTCTCCC TTCGGAGAGG GGTACATTCA AGAAGCGTGA
TATACTACTC CCTGTGAGTT GTATCGCCTT CTTCATGTGG ATATTTTGCA
CTACTTTTTT CAAGCGTTCT ATTGAACGCC TGATAATGAA AGTGTGTGCA    (SEQ ID NO. 2)
TATATCCGGG AGTGTACGGC GAAGGGACTC GGTCACTGGA AATTAATGTC
TCTATTGGGA CTTTAACTTC CAGGAGTTTC TTCAATGTGC ATTCTTTTTT
CCCACACCGT TATTTAAAC AACAAATCTG GATAGCGTTT GAGGGAAGAG
AAAGATGGTC TCTTTCTGTA TTTCTCTCTA TTCGCTTTCA GATTACTTAC
TAAAAACTAT AATGTTTTTC TAAATTTTCA GCAATGGA

FIG. 1.

```
                                    247 343               397
           64  73  96
        44 |              |       |            |    |                    |
EN 1   //─G─C─A─T─T─T─A─GC─C─A─T─T─TT─T─C─T─AA─A─T─//
BPA 1  //─A─T─C─T─T─T─A─GC─T─A─G─T─T─TT─T─AA─A─T─//
CN 1   //─A─T─C─T─T─T─A─GC─T─A─G─T─T─TT─T─AA─A─T─//
NC 1 GenBank U16160  //─A─T─C─T─T─T─A─GC─T─A─G─w─ky─kw─w─y─mw─m─k─//
NC 1 GenBank L49389  //─A─T─C─G─A─G─GC─T─C─G─T─TT─T─T─AA─A─T─//
```

FIG. 2.

EQUINE NEOSPORA ISOLATE AND ITS USES

CROSS-REFERENCE TO RELATED APPLICATIONS

Not applicable.

FEDERALLY SPONSORED RESEARCH AND DEVELOPMENT

Not applicable.

BACKGROUND OF THE INVENTION

This invention relates to the diagnosis and prevention of equine diseases caused by the protozoan parasite, Neospora. The invention specifically relates to isolated cultures of the parasite and nucleic acids and proteins isolated from them.

Neospora caninum, a cyst-forming parasite, was first reported to cause paralysis in young dogs (Bjerkas, et al., Acta Pathologica Microbiologia Immunologia Scandinavica 96:445 (1984); and Dubey, et al., J. Am. Vet. Med. Ass'n 192:1269 (1988)). Naturally occurring neonatal or fetal infections caused by Neospora-like protozoa have been described in cattle, deer, goats, horses and sheep (Barr, et al., J. Vet. Diag. Invest. 3:39 (1991); Woods, et al., J. Vet. Diag. Invest. 6:508 (1994); Barr, et al., J. Vet. Diag. Invest. 4:365 (1992); Dubey, et al., J. Parasitology 78:532 (1990); Gray, et at., J. Vet. Diag. Invest. 8:130 (1996); Marsh, et al., J. Am. Vet. Med. Ass'n 209:1907 (1996); Dalt, et al., Equine Vet. J. 1997; and Dubey, J. Protozoology 2:40 (1992)).

Since the discovery of the genus Neospora, successful isolation of these parasites from dogs and cattle have been reported (Dubey, et al., J. Am. Vet. Med. Ass'n 193:1259 (1988); Conrad, et al., Parasitology 106:239 (1993); Stenlund et al., Parasitology Res. 83:214 (1997); and Yamane, et al., Res. in Vet. Sci. 63:77 (1997)), and recently a Neospora sp. isolate was isolated from a neurologically impaired horse (Marsh, et al., J. Am. Vet. Med. Ass'n 209:1907 (1996)).

Previous characterization studies have failed to identify any distinct differences between the canine and bovine isolates of Neospora caninum (Marsh, et al., J. Parasitology 81:530 (1995); Stenlund, et al., Parasitology Res. 83:214 (1997); and Yamane, et al., Res. Vet. Sci. 63:77 (1997)). Prior to the work described herein, the ecuine Neospora isolate has not been characterized or immunochemically compared to the bovine or canine isolates.

Equine protozoal myeloencephalitis (EPM) is a neurological disease of horses. Symptoms of the disease include ataxia; weakness and spasticity, particularly of the hind legs; and difficulty controlling facial muscles. Secondary condition caused by EPM include, but are not limited to, muscle atrophy, loss of function, upward fixation of the patella, and back soreness.

Conventional thought has been that EPM is caused by Sarcocystis neurona. Sarcocystis falcatula also has been suggested as the causative agent of EPM, but from molecular data, this parasite may be the same as S. neurona. Until the elements of Koch's postulate are met, the relationship of these two parasites remains indeterminate.

Because Sarcocystis neurona does not encyst in the horse and enter a latent stage, EPM is treated as an acute infection with antiprotozoal and/or anti-inflammatory drugs, including trimethoprim plus sulfa or sulfadiazine with pyrimethamine.

Equine Neospora can only be treated during the acute stage, of the infection. Once cysts have formed in the afflicted animal, antiprotozoal drugs have no effect on the disease. Thus, Neospora infected horses must be treated early in the progression of the infection. Because the treatment of Neospora infection is different than the treatment of Sarcocystis neurona and because it is necessary to treat the afflicted animal immediately, diagnostic tools need to be developed which can distinguish the two parasites as soon as the afflicted animal shows symptoms of EPM.

To generate an assay capable of differentiating Neospora equi from Sarcocystis neurona, the more common etiologic agent of EPM, a more complete understanding of the identity and biology of Neospora-derived equine protozoal myeloencephalitis is necessary. This requires establishing continuous in vitro cultures of Neospora isolates. Such cultures would also be valuable in the development of pharmaceutical compositions for the treatment and prevention of Neospora infections. The present invention addresses these and other needs.

SUMMARY OF THE INVENTION

The present invention provides biologically pure cultures of equine Neospora. One such culture has been deposited with the ATCC and given ATCC Accession No. 209622 (NE 1). The NE1 isolate is listed in the National Animal Parasite Collection Log Book, kept by the U.S. Department of Agriculture, Agricultural Research Service as Accession No. 087601.00 and 087603.00.

The invention also provides methods of detecting the presence of antibodies specifically immunoreactive with an equine Neospora antigen in a biological sample (e.g., equine serum, cerebral spinal fluid, neurological tissue, or tissue culture medium). The method comprises contacting the sample with the Neospora antigen, thereby forming an antigen/antibody complex, and detecting the presence or absence of the complex. The Neospora antigen is an isolated Neospora tachyzoite, bradyzoite, oocyte or sporocyte protein. In addition, the antigen can be recombinantly produced. In some embodiments, the antigen is immobilized on a solid surface and the complex is detected using a fluorescently labeled anti-equine antibody.

The invention further provides methods of detecting the presence of Neospora in a biological sample. These methods comprise contacting the sample with an antibody specifically immunoreactive with a Neospora antigen, thereby forming an antigen/antibody complex, and detecting the presence or absence of the complex. The antibody (e.g., a monoclonal antibody) may be immobilized on a solid surface and the complex detected using a second labeled antibody. Typically, the biological sample is equine neurological tissue or fluid.

The methods of the invention also include detecting the presence of Neospora-specific nucleic acids in a biological sample by contacting the sample with a oligonucleotide probe which specifically hybridizes to a target Neospora-specific polynucleotide sequence and then detecting the presence or absence of the probe. In one embodiment of the invention, the methods further comprise amplifying the target Neospora-specific polynucleotide sequence.

The invention provides pharmaceutical compositions comprising a pharmaceutically acceptable carrier and an immunogenically effective amount of an equine Neospora antigen, such as a recombinantly produced equine Neospora polypeptide. The pharmaceutical compositions are used in protecting an equine animal from infection by equine Neospora. The pharmaceutical composition is usually administered parenterally.

Definitions

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv, F(ab), and F(ab)$_2$, as well as in single chains. Single-chain antibodies, in which genes for a heavy chain and a light chain are combined into a single coding sequence, may also be used.

"Biological sample" refers to any sample obtained from a living or dead organism. Examples of biological samples include biological fluids, tissue specimens and tissue culture media. Examples of tissue specimens include brain tissue, spinal cord, and placenta. Examples of biological fluids include blood, serum, plasma, urine, ascites fluid, cerebrospinal fluid and fetal fluid. "Neurological tissue" refers to a tissue sample from the central nervous system, including the brain and the spinal cord.

A "biologically pure equine Neospora culture" refers to a continuous in vitro culture of equine Neospora organisms (e.g., tachyzoites) which is substantially free of other organisms other than the host cells in which Neospora is grown. A culture is substantially free of other organisms if standard harvesting procedures (as described below) result in a preparation which comprises at least about 95%, preferably 99% or more of the organism, e.g., Neospora tachyzoites.

"Equine Neospora" refers to Neospora or "Neospora-like" protozoa identified in or isolated from equine tissues and fluids. Typically, the protozoal parasites are isolated from neurological tissue of horses. An exemplary isolate has been deposited with the American Type Culture Collection and has been given Accession No.209622.

An equine Neospora "protein" or "polypeptide" include allelic variations normally found in the natural population and changes introduced by recombinant techniques. Those of skill recognize that proteins can be modified in a variety of ways including the addition, deletion and substitution of amino acids.

"Nucleic acids" and "polynucleotides", as used herein, may be DNA or RNA. One of skill will recognize that for use in the expression of Neospora proteins or as diagnostic probes, polynucleotide sequences need not be identical but may be substantially identical to sequences disclosed here. In particular, where the inserted polynucleotide sequence is transcribed and translated to produce a functional polypeptide, one of skill will recognize that because of codon degeneracy, a number of polynucleotide sequences will encode the same polypeptide.

The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the sequence comparison algorithms listed below or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection.

For sequence comparison, typically one sequence acts as a reference sequence, to which test sequences are compared. When using a sequence, comparison algorithm, test and reference sequences are input into a computer, subsequence coordinates are designated, if necessary, and sequence algorithm program parameter, are designated.

The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul, et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: (1) the cumulative alignment score falls off by the quantity X from its maximum achieved value; (2) the cumulative score goes to zero or below, due to the accumulation of one or more negative-scoring residue alignments; or (3) the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the lest nucleic acid to the reference nucleic acid is less than about 0.1, more preferably less than about 0.01, and most preferably less than about 0.001.

An indication that two nucleic acid sequences are substantially identical is that the polypeptide encoded by the first nucleic acid is immunologically cross reactive with the polypeptide encoded by the second nucleic acid, as described below. In addition to being immunologically cross reactive, a two nucleic acid sequences are substantially identical if the two polypeptides are substantially identical, for example, where the two peptides differ only by conservative substitutions.

Another indication that polynucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically stringent conditions for a Southern blot protocol involve washing at room temperature with 0.1×SSC, 0.1% SDS.

One nucleic acid sequence is substantially identical to another nucleic acid sequence if the two sequences are products of PCR with identical primers. PCR with synthetic oligonucleotide primers and amplification of an RNA or DNA template is found in U.S. Pat. Nos. 4,683,195, 4,683,202, and PCR PROTOCOLS: A GUIDE TO METHODS AND APPLICATIONS (Innis et al., eds, 1990)). Methods such as polymerase chain reaction (PCR) and ligase chain reaction (LCR) can be used to amplify nucleic acid sequences of Neospora directly from mRNA, from cDNA, from genomic libraries or cDNA libraries. Degenerate oligonucleotides can be designed to amplify NE 1 homologues using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of nucleic acid sequences encoding mRNA in biological samples, for nucleic acid sequencing, or for other purposes. Genes amplified by the PCR reaction can be purified from agarose gels and cloned into an appropriate vector.

Proteins and polypeptides are substantially identical if, as mentioned above, they are immunoreactive. Immunoreactivity is determined by specific binding to an antibody generated against a defined immunogen, such as an immunogen derived from the NE 1 isolate of *Neospora equi*. Typically, this is done in an immunoassay using a polyclonal antiserum raised to the immunogen. This antiserum is selected to have low crossreactivity against other compounds and any such crossreactivity is removed by immunoabsorption prior to use in the immunoassay.

In order to produce antisera for use in an immunoassay, the immunogen is isolated as described herein. For example, recombinant protein may be produced in a mammalian cell line. An inbred strain of mice such as balb/c is immunized with the recombinant protein using a standard adjuvant, such as Freund's adjuvant, and a standard mouse immunization protocol (see Harlow & Lane, ANTIBODIES: A LABORATORY MANUAL, Cold Spring Harbor Pubs., N.Y. (1988)). Alternatively, a synthetic peptide derived from *N. equi* conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other proteins, using a competitive binding immunoassay such as the one described in Harlow & Lane, supra, at pages 570–573. For example, a protein isolated from cultured *N. equi* tachyzoites can be immobilized to a solid support. Proteins added to the assay compete with the binding of the antisera to the immobilized antigen. The ability of the above proteins to compete with the binding of the antisera to the immobilized protein is compared to the immunogen. The percent crossreactivity for the above proteins is calculated, using standard calculations. Those antisera with less than 10% crossreactivity with the protein listed above is selected and pooled. The cross-reacting antibodies are then removed from the pooled antisera by immunoabsorption with the immunogen.

The immunoabsorbed and pooled antisera are then used in a competitive binding immunoassay as described above to compare a second protein to the immunogen protein (e.g., a *Neospora equi* protein). In order to make this comparison, the two proteins are each assayed at a wide range of concentrations and the amount of each protein required to inhibit 50% of the binding of the antisera to the immobilized protein is determined. If the amount of the second protein required is less than twice the amount of the required immunogen, then the second protein is said to specifically bind to an antibody generated to the immunogen.

Substantially identical polypeptides or proteins include proteins with nonnatural mutations introduced deliberately with conventional recombinant technology such as single site mutation, or by excising short sections of DNA encoding Neospora proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring Neospora proteins. The biological properties of the altered proteins can be determined by expressing the protein in an appropriate cell line and measuring the immunogenic effect upon animals as described herein. Particular protein modifications considered minor would include conservative substitution of amino acids with similar chemical properties. By aligning a protein optimally with a protein of *N. equi* and by using the conventional immunoassays described herein to determine immunoidentity, one can determine substantially identical proteins of this invention.

The phrase "selectively hybridizing to", refers to a hybridization between a probe and a target sequence in which the probe binds substantially only to the target sequence when the target is in a heterogeneous mixture of polynucleotides and other compounds. Such hybridization is determinative of the presence of the target sequence. Although the probe may bind other unrelated sequences, at least 90%, preferably 95% or more of the hybridization complexes formed are with the target sequence.

The phrase "specifically immunoreactive with", when referring to a protein or peptide, refers to a binding reaction between the protein and an antibody which is determinative of the presence of the protein in the presence of a heterogeneous population of proteins and other compounds. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein and are described in detail below.

The phrase "substantially pure" or "isolated" when referring to a Neospora peptide or protein, means a chemical composition which is free of other subcellular components of the Neospora organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver staining. For certain purposes, high resolution is needed and HPLC or a similar means for purification can be utilized.

BRIEF DESCRIPTION OF THE DRAWINGS

FIG. 1 is the nucleotide sequence of the ITS 1 region of r-RNA from *Neospora equi* (FIG. 1A; SEQ ID NO:1) and the ITS 1 region of r-RNA from *Neospora caninum* (FIG. 1B; SEQ ID NO:2).

FIG. 2 is a schematic representation of the internal transcribed sequence showing the alignment of *Neospora equi* (NE 1) compared to sequences of *Neospora caninum* (BPA 1 and CN 1), and sequences of the NC-1 isolate (L49389 and U16160) available from GenBank. The boxed areas in this schematic show nucleotide sites that differ between isolates in the alignment. The nucleotide base number above each site is in reference to the *N. equi* sequence (SEQ ID NO:1).

DESCRIPTION OF THE PREFERRED EMBODIMENTS

The present invention provides Neospora cultures isolated from horse. The cultures are useful in a variety of applications including the production of nucleic acids or proteins for diagnostic assays and the preparation of immunogenic proteins for use in vaccine compositions.

I. Introduction

Tachyzoites of the *Neospora equi* isolate removed from an adult horse presenting with EPM were cultured to better characterize the protozoa. The tachyzoites were grown on a number of different stationary monolayer cultures, including but not limited to, monkey kidney (Vero) cells, human foreskin fibroblast (HS-68), bovine pulmonary artery endothelial (BPAE), and deer testes cells. The ultrastructural features of the NE 1 tachyzoite and bradyzoite in equine tissue were examined by electron microscopy. Antigenically, the zoites reacted strongly with antisera to Neospora species (bovine), weakly to antibodies directed against *Toxoplasma gondii*, and failed to react with antibodies directed against *S. neurona*. Based on the antigenic characteristics, it was determined the parasites from horse were similar to, but not identical to *Neospora caninum* and distinct from Toxoplasma.

Partial sequences of the nss-rRNA gene for the equine Neospora isolate (NE 1) were obtained and found to be identical to nss-rRNA from two *Neospora caninum* isolates (BPA 1 and CN 1). However, when compared the internal transcribed spacer (ITS 1) from the equine isolate (SEQ ID NO:1) and BPA 1 and CN 1 (SEQ ID NO:2), consistent sequence differences at specific nucleotide positions were seen. This difference indicated species divergence and that the isolated equine isolate of Neospora represented a distinct species from the protozoa that infect cattle and dogs.

As explained in detail below, the isolates are used to develop a variety of diagnostic assays as well as pharmaceutical compositions for treatment and prevention of Neospora infection.

I. Preparation of Neospora Polypeptides and Nucleic Acids

Standard protein purification techniques are used to isolate proteins from the tachyzoites or bradyzoites derived from the cultures provided herein. Such techniques include, but are not limited to, selective precipitation, column chromatography, and immunopurification methods. See, for instance, R. Scopes, PROTEIN PURIFICATION: PRINCIPLES AND PRACTICE, Springer-Verlag: New York (1982).

Using standard immunoblot techniques as described below, 3 unique proteins with molecular weights of approximately 63, 29, and 16 kilodaltons (kD) in equine Neospora lysates were identified. Standard protein purification methods were employed to purify these proteins and produce polyclonal or monoclonal antibodies for use in the diagnostic methods described below.

In an alternate embodiment, nucleic acids derived from the cultures are used for recombinant expression of the proteins. In these methods, the nucleic acids encoding the proteins of interest are introduced into suitable host cells, followed by induction of the cells to produce large amounts of the protein. This embodiment of the invention relies on routine techniques in the field of recombinant genetics, well known to those of ordinary skill in the art. A basic text disclosing the routine techniques is Sambrook, et al., MOLECULAR CLONING, A LABORATORY MANUAL, Cold Spring Harbor Publish., Cold Spring Harbor, N.Y. 2nd ed. (1989).

Nucleic acids for use as diagnostic oligonucleotide probes or for the recombinant expression of proteins are isolated using a number of techniques. For instance, fragments of proteins isolated from the cultures discussed above can be sequenced and used to design degenerate oligonucleotide probes for screening a cDNA library. Amino acid sequencing is performed and oligonucleotide probes are synthesized according to standard techniques as described, for instance, in Sambrook, et al., supra. Alternatively, oligonucleotide probes useful for identification of desired genes are also prepared from conserved regions of related genes in other species.

Polymerase chain reaction technology (PCR) is used to amplify nucleic acid sequences of the desired gene directly from mRNA, cDNA, genomic or cDNA libraries. Polymerase chain reaction (PCR) or other in vitro amplification methods are also useful, for example, to clone nucleic acid sequences that encode proteins to be expressed, to make nucleic acids to use as probes for detecting the presence of the mRNA in physiological samples, for nucleic acid sequencing, or for other purposes. For a general overview of PCR see PCR PROTOCOLS: A GUIDE TO METHODS AND APPLICATIONS, Innis, M, et al.,eds., Academic Press, San Diego (1990).

Standard transfection methods are used to produce prokaryotic, mammalian, yeast or insect cell lines which express large quantities of the desired polypeptide, which is then purified using standard techniques. See, e.g., Colley, et al., *J. Biol. Chem.* 264:17619–17622 (1989); and Scopes, supra.

In other aspects of this embodiment, the nucleotide sequences used to transfect the host cells are modified to yield Neospora polypeptides with a variety of desired properties. For example, the polypeptides vary from the naturally-occurring sequences at the primary structure level by amino acid insertions, substitutions, deletions, and the like. The amino acid sequence variants are prepared with various objectives in mind, including facilitation of purification and preparation of the recombinant polypeptide. The modified polypeptides are also useful for modifying plasma half life, improving therapeutic efficacy, and lessening the severity or occurrence of side effects during therapeutic use. The amino acid sequence variants are usually predetermined variants not found in nature but with the same immunogenic activity as naturally occurring protein.

In general, modifications of the sequences encoding the polypeptides may be readily accomplished by a variety of well-known techniques, such as site-directed mutagenesis (see, Gillman & Smith, *Gene* 8:81–97 (1979); and Roberts, et al., *Nature* 328:731–734 (1987)). One of ordinary skill will appreciate that the effect of many mutations is difficult to predict. Thus, most modifications are evaluated by routine screening in a suitable assay for the desired characteristic. For instance, the effect of various modifications on the ability of the polypeptide to elicit a protective immune response is easily determined using in vitro assays. More specifically, the polypeptides are tested for heir ability to induce lymphoproliferation, T cell cytotoxicity, or cytokine production using standard techniques.

The particular procedure used to introduce the genetic material into the host cell for expression of the polypeptide is not critical. Any of the well known procedures for introducing foreign nucleotide sequences into host cells may be used. These include the use of calcium phosphate transfection, spheroplasts, electroporation, liposomes, microinjection plasmid vectors, viral vectors and any of the other well known methods for introducing cloned genomic DNA, cDNA, synthetic DNA or other foreign genetic material into a host cell (see Sambrook, et al., supra). It is only necessary that the particular procedure utilized be capable of successfully introducing at least one gene into the host cell which is capable of expressing the gene.

Any of a number of well known cells and cell lines are used to express the polypeptides of the invention. For instance, prokaryotic cells such as *E. coli* are used. Eukaryotic cells include, but are not limited to, yeast, Chinese hamster ovary (CHO) cells, human embryonic kidney (HEK) cells, COS cells, and insect (Lepidoptera) cells.

The particular vector used to transport the genetic information into the cell is also not critical. Any of the conventional expression vectors used for expression of recombinant proteins in prokaryotic and eukaryotic cells are used in this invention.

Expression vectors typically contain a transcription unit or expression cassette containing all the elements required for the expression of the DNA encoding a polypeptide by the host cells. A typical expression cassette contains a promoter operably linked to the DNA sequence encoding a polypeptide and signals required for efficient polyadenylation of the transcript. The term "operably linked" as used herein refers to linkage of a promoter upstream from a DNA sequence. The promoter mediates transcription of the DNA sequence and is preferably positioned about the same distance from the heterologous transcription start site as it is from the transcription start site in its natural setting. As is known in the art, however, some variation in this distance is accommodated without loss of promoter function. Other regulatory elements including splice donor and acceptor sequences are optimally within an expression cassette. In addition to an expression cassette, an expression vector comprises sequences which confer a selectable phenotype to successfully transformed or transfected cell lines. Such sequences include, but are not limited to, neo, dhfr, and mdr.

Following the growth of the recombinant cells and expression of the polypeptide, the culture medium is harvested for purification of the secreted protein. Typically, the media are clarified by centrifugation or filtration to remove cells and cell debris. The proteins in the supernatant are concentrated by adsorption to any suitable resin or by use of ammonium sulfate fractionation, polyethylene glycol precipitation, or by ultrafiltration. Other routine means known in the art are equally suitable. Further purification of the polypeptide to homogeneity is accomplished by standard techniques, for example, affinity chromatography, ion exchange chromatography, sizing chromatography, $His_6$ tagging and Ni-agarose chromatography (as described in Dobeli, et al., *Mol. and Biochem. Parasit.* 41:259–268 (1990)), or other protein purification techniques. The purified proteins are then used in the diagnostic assays and to produce pharmaceutical compositions, both of which are described below.

An alternative method of preparing recombinant polypeptides useful as vaccines involves the use of recombinant viruses (e.g., vaccinia). Vaccinia virus is grown in suitably cultured mammalian cells such as the HeLa S3 spinner-adapted cells, as described by Mackett, et al., in DNA CLONING VOL. II. A PRACTICAL APPROACH, D. M. Glover (Ed.), IRL Press, Oxford, pp 191–211.

III. Antibody Production

In another embodiment of this invention, the isolated proteins or cultures of the present invention are used to produce antibodies specifically reactive with Neospora antigens, including proteins. However, it is not necessary for the antigens to be proteinaceous; carbohydrates or other compounds present in *Neospora equi* can be used. If isolated proteins are used, they are either recombinantly produced or isolated from Neospora cultures as described above. Synthetic peptides made by methods well known in the art using the protein sequences are also encompassed within this embodiment.

Methods of polyclonal antibody production are known to those of skill in the art. In brief, an immunogen, preferably a purified protein, is mixed with an adjuvant and animals are immunized. When appropriately high titers of antibody to the immunogen are obtained, blood is collected from the animal and antisera are prepared. Further fractionation of the antisera to enrich for antibodies reactive to Neospora proteins is done if desired. (See Harlow & Lane, ANTIBODIES: A LABORATORY MANUAL, Cold Spring Harbor Pubs., New York (1988)).

Animals were immunized with the NE 1 isolate of *Neospora equi* to generate polyclonal antisera. The polyclonal antisera were used to identify and characterize Neospora tachyzoite and bradyzoite stages in the tissues of infected animals using, for instance, immunoperoxidase test procedures as described in Anderson, et al., *J. Am. Vet. Med. Ass'n* 198:241 (1991);and Barr, et al., *Vet. Pathol.* 28:110–116(1991).

Monoclonal antibodies are obtained by various techniques familiar to those skilled in the art. Briefly, spleen cells from an animal immunized with a desired immunogen are immortalized, commonly by fusion with a myeloma cell (See, Kohlei & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the desired antigen.

In one aspect of this embodiment, the NE 1 isolate is used to immunize mice to obtain sensitized B cells for hybridoma production. With these cells, monoclonal antibodies to equine Neospora immunogens are obtained. The monoclonal antibodies are used, for instance, in ELISA diagnostic tests, immunohistochemical tests, for the in vitro evaluation of parasite invasion, to select candidate antigens for vaccine development, protein isolation, and for screening genomic and cDNA libraries to select appropriate gene sequences.

IV. Diagnosis of Neospora Infections

The present invention also provides methods for detecting the presence or absence of Neospora in a biological sample. Because Neospora and Sarcocystis infections cause similar symptoms, but are treated differently, a diagnostic test which differentiates these two parasitic protozoa is needed. In one embodiment of this invention, antibodies specifically reactive with Neospora are detected using either proteins or the Neospora isolates described herein. The proteins and isolates can also be used to raise specific antibodies (either monoclonal or polyclonal) to detect the antigen in a sample. In addition, the nucleic acids disclosed and claimed herein are used to detect Neospora-specific sequences using standard hybridization techniques. Each of these types of assays is described below.

A. Immunoassays

For a review of immunological and immunoassay procedures in general, see BASIC AND CLINICAL IMMUNOLOGY 7TH ED. (D. Stites and A. Terr ed.) 1991. The immunoassays of the present invention are performed in any of several configurations, which are reviewed extensively in ENZYME IMMUNOASSAY, E. T. Maggio, ed., CRC Press, Boca Raton, Fla. (1980); and LABORATORY TECHNIQUES IN BIOCHEMISTRY AND MOLECULAR BIOLOGY, P. Tijssen, Elsevier Science Publishers B. V. Amsterdam (1985). For instance, the proteins and antibodies disclosed herein are conveniently used in ELISA, immunoblot analysis and agglutination assays.

In brief, immunoassays to measure anti-Neospora antibodies or antigens are either competitive or noncompetitive binding assays. In competitive binding assays, the sample analyte (e.g., anti-Neospora antibodies) competes with a labeled analyte (e.g., anti-Neospora monoclonal antibody) for specific binding sites on a capture agent (e.g., isolated Neospora protein) bound to a solid surface. The concentration of labeled analyte bound to the capture agent is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means.

A number of combinations of capture agent and labeled binding agent are contemplated. For instance, an isolated Neospora protein or culture is used as the capture agent and labeled anti-equine antibodies specific for the constant region of equine antibodies are used as the labeled binding agent. Goat, sheep and other non-equine antibodies specific for equine immunoglobulin constant regions (e.g., $\gamma$ or $\mu$) are well known in :he art. Alternatively, the anti-equine antibodies are the capture agent and the antigen is labeled.

Various components of the assay, including the antigen, anti-Neospora antibody, or anti-equine antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component is then covalently bound or noncovalently attached to the solid substrate through nonspecific binding.

Alternatively, the immunoassay is carried out in liquid phase and a variety of separation methods are employed to separate the bound labeled component from the unbound labeled components. These methods are known to those of skill in the art and include, but are not limited to, immunoprecipitation, column chromatography, adsorption, addition of magnetizable particles coated with a binding agent and other similar procedures.

In another alternate procedure, an immunoassay is carried out in liquid phase without a separation procedure. Typically, in these procedures, the assayed protein or other analyte competes with a compound for binding to an antibody attached to a label. The binding of the analyte to an antibody, but not the binding of the compound to the antibody, causes a change in the signal emitted by the label, so that analyte binding is measured without separating the bound from the unbound labeled component.

Western blot (immunoblot) analysis is also used to detect the presence of antibodies to Neospora in a biological sample. This technique is a reliable method for confirming the presence of antibodies against a particular protein in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labeled anti-equine antibodies.

The immunoassay formats described above employ labeled assay components. The label is in a variety of forms. The label is coupled either directly or indirectly to the desired component of the assay according to methods well known in the art. A wide variety of labels is available and the component may be labeled by any one of several methods. Traditionally a radioactive label incorporating $^{3}H$, $^{125}I$, $^{35}S$, $^{14}C$, or $^{32}P$ is used. Non-radioactive labels include ligands which bind to labeled antibodies; fluorophores, chemiluminescent agents, enzymes, and antibodies which can serve as specific binding pair members for a labeled ligand. The choice of label depends on sensitivity required, ease of conjugation with the compound, stability requirements, available instrumentation, and the preference of the operator.

Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see U.S. Pat. No. 4,391,904.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands are available. Where a ligand has a natural anti-ligand, for example, biotin, thyroxine, and cortisol, it are used in conjunction with the labeled, naturally occurring anti-ligands. Alternatively, any haptenic or antigenic compound can be used in combination with an antibody.

Some assay formats do not require the use of labeled components. For instance, agglutination assays are used to detect the presence of the target antibodies. In this case, antigen-coated particles are agglutinated by samples comprising the target antibodies. In this format, none of the components need be labeled and the presence of the target antibody is detected by simple visual inspection. If necessary, visualization can be microscopically.

B. Detection of Neospora Nucleic Acids

As noted above, this invention also embraces methods for detecting the presence of Neospora DNA or RNA in biological samples. These sequences are used to detect all stages of the Neospora life cycle (e.g., tachyzoites, bradyzoites, and oocysts) in biological samples from both the equine host and the definitive host. A variety of methods of specific DNA and RNA measurement using nucleic acid hybridization techniques are known to those of skill in the art. See, Sambrook, et al., supra.

One method for determining the presence or absence of Neospora DNA in a sample involves a Southern transfer. Briefly, digested DNA is run on agarose slab gels in buffer and transferred to membranes. In a similar manner, a northern transfer may be used for the detection of Neospora mRNA in samples of RNA. Hybridization is carried out using labeled oligonucleotide probes which specifically hybridize to Neospora nucleic acids. Labels used for this purpose are generally as described for immunoassays. Visualization of the hybridized portions allows the qualitative determination of the presence or absence of Neospora genes.

A variety of other nucleic acid hybridization formats are known to those skilled in the art. For example, common formats include sandwich assays and competition or displacement assays. Hybridization techniques are generally described in NUCLEIC ACID HYBRIDIZATION, A PRACTICAL APPROACH, Hades, B. D. & Higgins, S. J. (Eds.), IRL Press, 1985; Gall & Pardue, *Proc. Natl. Acad. Sci., U.S.A.* 63:378–383 (1969); and John, et al., *Nature* 223:582–587 (1969).

Sandwich assays are commercially useful hybridization assays for detecting or isolating nucleic acid sequences. Such assays utilize a "capture" nucleic acid covalently immobilized to a solid support and labeled "signal" nucleic acid in solution. The biological sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods described in the art are the nucleic acid sequence based amplification (NASBATM, Cangene, Mississauga, Ontario) and Q Beta Replicase systems.

An alternative means for detecting Neospora nucleic acids is in situ hybridization. In situ hybridization assays are well known and are generally described in Angerer, et al., *Methods Enzymol.* 152:649–660 (1987). In situ hybridization assays use cells or tissue fixed to a solid support, typically a glass slide. If DNA is to be probed, the cells are denatured with heat or alkali. The cells are then contacted with a hybridization solution at a moderate temperature to permit annealing of labeled Neospora specific probes. The probes are preferably labeled with radioisotopes or, more preferably with, fluorescent reporters.

Exemplary nucleic acid sequences for use in the assays described above include sequences from the nss-rRNA and ITS 1 sequences disclosed herein. For instance, the primer and probe sequences disclosed in Example 3 are used to amplify and identify nucleic acids of equine Neospora in blood, cerebrospinal fluid and other tissue, as well as in frozen or formalin-fixed tissue. These primers are particularly useful for the diagnosis of neosporosis and identification of the source of Neospora parasite stages (tachyzoites, bradyzoites and oocysts) in other animal hosts.

V. Pharmaceutical Compositions Comprising Anti-Neospora Antibodies and/or Neospora Immunogens In another embodiment, a pharmaceutical composition for the treatment and/or prevention of Neospora infections is prepared using anti-Neospora monoclonal antibodies or fragments thereof as well as Neospora proteins or their immunogenic equivalents. The phrase "pharmaceutical compositions" refers to a composition which is administered to an animal to elicit a reduction in a pathological condition. For purposes of this invention, it encompasses veterinary compositions used to treat and/or prevent neosporosis and EPM.

The proteins or other Neospora antigens of this invention are used to raise antibodies. Antibody compositions are particularly useful for parenteral administration, such as intravenous administration or administration into a body cavity or lumen of an organ. For example, EPM may be treated by intravenous administration or by localized delivery of the antibody to the cerebrospinal fluid or directly into the brain.

The compositions for administration commonly comprise a solution of the antibody dissolved in a pharmaceutically acceptable carrier, preferably an aqueous carrier. A variety of aqueous carriers are used, e.g., buffered saline and the like. These solutions are sterile and generally free of undesirable matter. These compositions are sterilized by conventional, well known sterilization techniques. The compositions contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, and sodium lactate. The concentration of antibody in these formulations varies widely, and will be selected primarily based on fluid volumes, viscosities, and body weight in accordance with the particular mode of administration and the animal's needs.

Thus, a typical pharmaceutical antibody composition of the present invention for intravenous administration is about 0.1 to 10 mg per animal per day. Dosages from 0.1 up to about 100 mg per animal per day may be used, particularly if the antibody is administered to a secluded site and not into the circulatory or lymph system, such as into the cerebrospinal fluid or the brain. Actual methods for preparing administrable compositions will be known or apparent to those skilled in the art and are described in more detail in veterinary pharmaceutical publications, or such publications like REMINGTON'S PHARMACEUTICAL SCIENCE, 19TH ED., Mack Publishing Company, Easton, Pa. (1995).

The compositions of the present invention can be administered for therapeutic applications. In therapeutic applications, compositions are administered to an animal suffering from a disease caused by *Neospora equi*, for example EPM, in an amount sufficient to cure or at least partially arrest the disease and its complications. An amount adequate to accomplish this is defined as a "therapeutically effective dose." Amounts effective for this use will depend upon the severity of the disease and the general state of the animal's health. An effective amount of the composition provides either subjective relief of a symptom(s) or an objectively identifiable improvement as noted by the veterinarian or other qualified observer.

Single or multiple doses of the compositions are administered depending on the amount and frequency required and tolerated by the animal. In any event, the composition should provide a sufficient quantity of the compounds of this invention to effectively treat the afflicted animal. Preferably, the composition is administered once but may be applied periodically until either a therapeutic result is achieved or until side effects warrant discontinuing therapy. Generally, the dose is sufficient to treat or ameliorate symptoms or signs of disease without producing unacceptable toxicity to the animal.

Controlled release parenteral formulations of the compositions are made as implants, oily injections, or as particulate systems. For a broad overview of delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa. (1995). Particulate systems include microspheres, microparticles, microcapsules, nanocapsules, nanospheres, and nanoparticles. Microcapsules contain a compound as a central core. In microspheres the compound is dispersed throughout the particle. Particles, microspheres, and microcapsules smaller than about 1 $\mu$m are generally referred to as nanoparticles, nanospheres, and nanocapsules, respectively. Capillaries have a diameter of approximately 5 $\mu$m so that only nanoparticles are administered intravenously. Microparticles are typically around 100 $\mu$m in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219–342 (1994); and Tice & Tabibi, TREATISE ON CONTROLLED DRUG DELIVERY, A. Kydonieus, ed., Marcel Dekker, Inc. New York, N.Y., pp.315–339, (1992).

Polymers can be used for ion-controlled release of pharmaceutical compositions. Various degradable and nondegradable polymeric matrices for use in controlled drug delivery are known in the art (Langer, R., *Accounts Chem. Res.* 26:537–542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425–434 (1992); and Pec, et al., *J. Parent. Sci. Tech.* 44(2):58–65 (1990)). Alternatively, hydroxyapatite has been used as a microcarrier for controlled release of proteins (Ijntema, et al., *Int. J. Pharm.* 112:215–224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496.

In addition to the use of therapeutic compositions, an embodiment of this invention is the use of Neospora or Neospora compounds as vaccines. The vaccines are used to immunize horses, cattle, sheep, goats and other animals from infection by Neospora. The compositions of the invention are also used to treat a definitive host to prevent the shedding of oocysts and subsequent transfer to horses and other animals. The compositions for administration to either horses or the definitive host can comprise tachyzoite and/or bradyzoite immunogens.

The vaccine is used to raise a humoral or a cell-mediated immune response and preferably both. Experimental evidence indicates that cell-mediated immunity (CMI) is an important component of the protective immune response in horses. A variety of methods for evaluating the specificity of the helper and cytotoxic T cell response to selected antigens in vitro are used to evaluate CMI.

The vaccines of the invention are typically administered orally or parenterally, usually intramuscularly or subcutaneously. For parenteral administration, the immunogen is combined with a suitable carrier. For example, it is administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Bordetella pertussis*, and the like. Such adjuvants are available commercially from various sources, for example, Merck Adjuvant 6 (Merck and Company, Inc., Rahway, N.J.). Other suitable adjuvants are MPL+TDM Emulsion (RIBBI Immunochem Research Inc. U.S.A.). Other immuno-stimulants include interleukin 1, interleukin 2 and interferon-gamma.

Proteins immunogens are provided either as a vaccine or their corresponding genetic sequence is provided as a functional operon with a recombinant vaccine system such as vaccinia virus. The proportion of immunogen and adjuvant are varied over a broad range so long as both are present in effective amounts.

Vaccine compositions of the invention are administered to an animal susceptible to Neospora infection, including but not limited to, a horse, cow, sheep, or goat, to elicit an immune response against the antigen and thus enhance the animal's own immune response capabilities. Such an amount is defined to be an "immunogenically effective amount." The precise amount depends on the judgement of the prescribing veterinarian and includes consideration of the animal's state of health and weight, the mode of administration, the nature of the formulation, and the like. Generally, on a per-dose basis, the concentration of the Neospora immunogen ranges from about 1 $\mu$g to about 100 mg per equine host. For administration to horses, a preferable range is from about 100 $\mu$g to about 1 mg per unit dose.

A suitable dose size is about 1–10 mL, preferably about 1.0 mL. Accordingly, a typical dose for subcutaneous injection, for example, comprises 1 to 2 mL containing 0.1 to 10 mg of immunogen.

A variety of vaccination regimens are effective in immunizing, horses and other animals. Preferably, fillies and mares are vaccinated just prior to, or all the time of breeding so as to prevent abortion and reduce the possibility of congenital infections. A second immunization is given 2–4 weeks after initial immunization. Colts and adult males are vaccinated at any time. Animals that have been previously exposed to Neospora or have received colostral antibodies from the mare may require booster injections. The booster injection is preferably timed to coincide with times of maximal challenge. Different immunization regimes may be adopted depending on the judgment of the veterinarian.

Vaccines of the invention may comprise a crude extract of Neospora tachyzoites, bradyzoites or other stages of the protozoan's life cycle. Chemically fixed parasites or cells can also be used. As noted above, preferred vaccines comprise partially or completely purified Neospora protein preparations. The antigen produced by recombinant DNA technology is preferred because it is more economical than the other sources and is more readily purified in large quantities.

In another aspect of prophylaxis, isolated Neospora gene sequences are used to transform viruses that transfect host cells in animals. Live attenuated viruses, such as vaccinia or adenovirus, are convenient alternatives for vaccines because they are inexpensive to produce and are easily transported and administered.

Suitable viruses for use in the present invention include, but are not limited to, pox viruses, such as capripox and cowpox viruses, and vaccinia viruses, alpha viruses, adenoviruses, and other animal viruses. The recombinant viruses are produced by methods well known in the art, for example, homologous recombination or ligation of two plasmids. A recombinant canarypox or cowpox virus is made, for example, by inserting the DNA encoding the Neospora protein or fragments into plasmids so that they are flanked by viral sequences on both sides. The DNA encoding Neospora polypeptides are then inserted into the virus genome through homologous recombination.

Preferentially, a viral vaccine using recombinant vaccinia virus is used. A vaccine prepared utilizing the gene encoding the Neospora protein incorporated into vaccinia virus would comprise stocks of recombinant virus where the gene encoding the Neospora protein is integrated into the genome of the virus in a form suitable for expression of the gene.

EXAMPLES

Example 1

This example describes the ultrastructural characterization of Neospora parasites isolated from equine spinal cord.

As previously described (Marsh, et al., *J. Am. Vet. Med. Ass'n* 209:1907–1913 (1996)), spinal cord containing parasites was fixed by placing it in a modified Karnovsky's fixative (1% paraformaldehyde in 2% glutaraldehyde with 0.1 M sodium cacodylate and 0.001 M calcium chloride at pH 7.4) for 24 hours. The tissue was washed twice with 0.2 M sodium cacodylate at pH 7.4, 20 minutes per wash, before a postfixation bath for 1 hour in unbuffered 2% osmium tetroxide reduced with 2.5% potassium ferrocyanide. The tissue was dehydrated through a series of graded ethanol baths, transitioned through propylene oxide, infiltrated and embedded in a 1:1 mixture of Eponate® 12 and Spurr's low viscosity resin (both from Ted Pella, Inc., Redding, Calif.). One micron sections were cut, mounted on glass coverslips and stained by toluidine blue for light microscopic examination.

For transmission electron microscopy, thin sections (70–90 nm) were prepared on a Reichert Ultracut E ultramicrotome (Leica, Deerfild, Ill.) and placed on 300 mesh copper grids before staining with 2% aqueous uranyl acetate for 1 hour at 60° C. on parafilm (American National Can, Greenwich, Conn.) over wet filter paper in a petri dish. Sections were post-stained for 10 minutes in Reynold's lead citrate before examination in a Zeiss 10C transmission electron microscope (LEO Electron Microscope, Inc., Thornwood, N.Y.) at 80 kv accelerating voltage (Reynolds, *J. Cell. Biol.* 17:208–212 (1963)).

The ultrastructural features seen in the tachyzoites of the equine isolate were distinctive for Neospora species zoites. These features included the uniform electron dense staining pattern of rhoptries compared to the "spongy" pattern described for *T. gondii* (Lindsay, et al., *Am. J. Vet. Res.* 54:103–106 (1993)), the presence of several electron dense granules both posterior and anterior to the tachyzoite nuclei, and the presence of micronemes oriented parallel or perpendicular to the pellicle of the zoites (Bjerkas, et al., *Acta Path. Microbiol. Immunol. Scandinavica* 96:445–454 (1988); Barr, et al., *J. Vet. Diag. Invest.* 3:3946 (1991); Dubey, et al., *J. Am. Vet. Med. Ass'n* 193:1259–1263 (1988); and Speer, et al., *J. Protozoology* 36:458–463 (1989))

The ultrastructure of the protozoal cysts in the spinal cord also were compatible with the genus Neospora sp. with the exception that the cyst wall were varied in width but often were thinner compared to previous ultrastructural characterization studies of *N. caninum* (bovine and canine origin) (Levine, VETERINARY PROTOZOOLOGY, Ames, Ia.: Iowa State University Press, pp13–15 (1985); and Speer, et al., *J. Protozoology,* 36:458–463 (1989)).

Example 2

This example describes the cultivation of *Neospora equi* isolated from horse and the preparation of tachyzoite protein and nucleic acid compositions.

The NE 1 equine Neospora sp. isolate (Marsh, et al., *J. Am. Vet. Med. Ass'n* 209:1907–1913 (1996)) was grown in deer testes cells with protozoal culture media consisting of Dulbecco's Minimum Essential Medium (Gibco/BRL, Gaithersburg, Md.) supplemented with 10% (v/v) heat-inactivated fetal bovine serum, 2 mM L-glutamine, 50 U/mL penicillin and 50 µg/mL streptomycin.

The *Neospora caninum* isolate (CN 1) was cultured from the brain and spinal cord of a 6 week old Rhodesian Ridgeback pup born with neurological symptoms of neosporosis. The pup also had a *Neospora caninum* indirect fluorescent antibody test titer (Conrad, et al., *Parasitology* 106:239–249 (1993)) of 1:10,240 when tested at 6 weeks of age. At the time of euthanasia, the canine was moribund with very poor body condition and was reluctant to stand. Following euthanasia, a complete necropsy was performed on the dog and tissues were processed for histology and immunohistochemistry as previously described. (Barr, et al., *Lab. Invest.* 71:236–242 (1994)). Neurological tissues were processed and cultures were maintained as described (Conrad, et al., *Parasitology* 106:239–249 (1993)) except that primary isolation was on Vero cell monolayers.

The CN 1 isolate isolated from the pup was initially characterized and found to be consistent with other canine and bovine *N. caninum* isolates based on morphologic, antigenic, and molecular criteria. The tachyzoites divided by endodyogeny and reacted strongly to anti-*N. caninum* antibodies and weakly to *T. gondii* antibodies.

The BPA 1 isolate from an aborted bovine fetus (Conrad, et al., *Parasitology* 106:239–249 (1993)) was used to represent bovine-derived *N. caninum* since no molecular (Marsh, et al., *J. Parasitology* 81:530–535 (1995)) or morphological (Yamane, et al., *Res. Vet. Sci.* 63:77–80 (1997)) differences have been detected between bovine Neospora isolates to date. Parasites were grown in Vero cell monolayers similar to conditions described for NE 1 and CN 1 isolates.

Viable tachyzoites from the two *N. caninum* isolates (CN 1 and BPA 1) and from the equine Neospora sp. isolate (NE 1) were harvested from similarly infected and maintained monolayers when approximately 70% of the monolayer cells had visible clusters of intracellular tachyzoites. Harvesting was accomplished by scrapping the monolayers vigorously with a cell scraper to release most of the intracellular tachyzoites into the culture media. The culture media containing cells and tachyzoites was centrifuged al 150033 g, and the pellet was resuspended in phosphate-buffered saline (PBS). This suspension was expressed through a 22-gauge needle three times and filtered through a sterile 5 µm polycarbonate filter. The parasite containing eluate was then centrifuged at 1500×g for 10 minutes at room temperature (22–24° C.). The supernatant was removed and the pellet was washed twice with PBS. Uninfected Vero cell monolayer cultures were treated in the same way to serve as a negative control in subsequent protein and DNA analysis studies. The resulting pellets were stored at −70° C. until used.

Antibody Production

For preparation of polyclonal antibodies to the NE 1 tachyzoiles, a female rabbit was immunized by subcutaneous and intramuscular injection over the course of 106 days with $10^5$ to $10^6$ tachyzoites. Preimmune serum was drawn 1 day prior to the first immunization, and terminal blood was collected 7 days after the final inoculation. Polyclonal antibodies to the bovine Neospora isolate, BPA 1 (Conrad, et al., *Parasitology* 106:239–249 (1993)) were obtained as previously described (Barr, et al., *Lab. Invest.* 71:236–242 (1994)). Monoclonal antibodies from culture supernatants were produced against *N. caninum* isolate, CN 1, by commonly used methods.

Protein Analysis

Thawed tachyzoite pellets and control uninfected Vero cells were boiled for 5 minutes in either reducing (containing 10% β-mercaptoethanol) or non-reducing SDS-PAGE sample application buffer. Solubilized proteins from the tachyzoites and Vero cells were electrophoresed through a 4% polyacrylamide stacking gel (pH 6.8) followed by a 12% polyacrylamide separating gel or continuous 4–10% gradient gel (pH 8.8). Prestained SDS-PAGE low molecular weight standards (Bio-Rad, Hercules, Calif.) were included with each gel.

After electrophoretic separation, the proteins were transferred to nitrocellulose membranes (BioRad) which were blocked with phosphate buffered saline (PBS) containing 5% w/v nonfat dry milk and then incubated with the primary antibody for 18 hours at 4° C. The primary antibodies were polyclonal antisera raised against the BPA 1 isolate (Barr, et al., *Lab. Invest.* 71:236–242 (1994)), and the NE1 isolate, which were diluted at 1:300, and the CN 1 monoclonal antibodies, which were diluted at 1:0. The corresponding preimmune rabbit sera at the same dilutions served as negative controls. Goat anti-rabbi, IgG (H+L) labeled with peroxidase (Jackson ImmunoResearch Inc, West Grove, Pa.) or goat anti-mouse IgG labeled with peroxidase (Amersham, Arlington Heights) was used as the secondary antibody. After washing, the blots were processed for 4-chloro-1-napthol color development or chemiluminescence (monoclonal antibodies only) for signal development.

If chemiluminescence labels were used, after signal development, the blots were rinsed one time in TBS (10 mM Tris-HCl, 150 mM NaCl). The blots were then processed for color development using diaminobenzidine substrate with nickel ion enhancement (Harlow, et al., ANTIBODIES: A LABORATORY MANUAL, Cold Spring Harbor, N.Y.: Cold Spring Harbor Laboratory, pp496–508 (1988)).

The rabbit anti-*N. caninum* (BPA 1) polyclonal antibodies reacted with a number of shared proteins in all the parasite lysate preparations but demonstrated no reactivity to the Vero monolayer lysate. Two distinct proteins of approximate molecular weight of 70 and 42 kD of the *N. equi* preparation reacted with the antiserum to *N. caninum*. These two proteins were not detected in the *N. caninum* parasite lysates. In contrast, the *N. caninum* lysates (BPA 1 and CN 1) contained several proteins, with approximate molecular weights of 67, 40, 33, 27 and 18 kD, which reacted to the *N. caninum* antiserum but were not detected in the *N. equi* parasite lysate.

The rabbit anti-NE 1 antibodies reacted with a number of shared proteins in all the parasite lysate preparations and with two proteins of approximate molecular weight of 59 and 25 kD derived from the Vero monolayer lysate. Three unique proteins; of approximate molecular weight of 63, 29, and 16 kD of the *N. equi* lysate preparations reacted with the antiserum against *N. equi*. This antiserum also detected three unique proteins of approximate molecular weight of 45, 38, and 33 kD in the *N. caninum* parasite lysates.

The reactivity of two monoclonal antibodies to the *N. equi* and *N. caninum* isolates were distinctly different. One of the monoclonal antibodies recognized a protein of approximately 35.4 kD in the *N. equi* isolate. Similarly, the same monoclonal antibody reacted with a protein of approximately 34 kD in the *N. caninum* preparations. The other monoclonal antibody did not react with the *N. equi* preparation; however, it recognized an approximately 26 kD protein in the *N. caninum* preparations. Neither monoclonal antibody reacted with the Vero cell control antigens.

Example 3

This example describes the differences in the genome of the *N. equi* and the *N. caninum* isolates.

The ITS 1 region of genomic DNA was chosen for evaluation because this DNA sequence had been proven useful in studies on the evolutionary biology of populations and species, and sequence data for multiple *N. caninum* isolates (CN 1 and NC-Liv) were available (Stenlund, et al., *Parasitology Res.* 83:214–219 (1997)). It was found that there were no differences in the ITS 1 region of different *N. caninum* isolates.

Genomic DNA was isolated from the three isolates, NE 1, CN 1, and BPA 1, and the Vero cell monolayer (negative control) using the IsoQuick DNA extraction kit (Orca, Bothell, Wash.). The polymerase chain reaction (PCR) was used to amplify the nuclear small subunit (nss)-rRNA DNA as previously described (Marsh, et al., *J. Parasitology* 81:530–535 (1995)) and the internal transcribed spacer (ITS 1) sequence was amplified using primers derived from the bovine Neospora ITS 1 region:

5' GGAAGTAAAAGTCGTAACAAGG 3' (SEQ ID NO:3) and

5' GCTGCGTTCTTCATCGATGC 3' (SEQ ID NO:4). The PCR amplification products were purified as described (Marsh, et al., *J. Parasitology* 81:530–535 (1995)) to obtain a DNA template for subsequent DNA sequencing reactions. This method had been found to be advantageous in that it does not select a single cloned fragment, thus eliminating mistakes due to the Taq polymerase or intraspecific polymorphisms in the ITS 1.

Automatic sequencing reactions were performed using the recommended protocol provided by the manufacturer of the ABI Prism 377 (Applied Biosystems, Perkin-Elmer, Foster City, Calif.). The sequencing of the nss-rRNA subunit used primers as previously described (Marsh, et al., *J. Parasitology* 81:530–535 (1995)) while sequencing of the ITS 1 region used SEQ ID NO:3, SEQ ID NO:4, and two additional internal primers, 5' CTCCTTCG-GAGAGGGGTA 3' (SEQ ID NO:5) and 5' TCTTCCCT-CAAACGCTATC 3' (SEQ ID NO:6).

Final DNA sequence construction, alignments, and comparisons were facilitated using a VMS system (Digital Equipment Corporation, Maynard, Mass.) on a VAX 8600 with the GCG programs. The DNA sequences for the nss-rRNA gene were compared to the published sequence for the BPA 1 isolate (U17345, GenBank). The DNA sequences for the ITS 1 region were compared to the published sequence for *N. caninum (NC-Liverpool,* U16159, Genbank), *N. caninum* (NC-1 L49389, GenBank), and *N. caninum* (NC-1 U16160, GenBank). The aligned Neospora spp. sequences were trimmed to the limits of the NE 1 sequence (nss-rRNA gene, 1686 nucleotides) and (ITS 1, 438 nucleotides; SEQ ID NO: 1), and this data set was used for the analysis.

No differences were found in the nss-rRNA gene sequence of *N. equi* as compared to the sequences of *N. caninum* isolates (BPA 1 and NC 1). However, comparison of the ITS 1 region revealed consistent sequence differences between the *N. equi* and the four *N. caninum* isolates (CN 1, NC-1, NC-Liv, and BPA 1) at nucleotide positions (nt) 44, 64, 73, 96, 247, 343, and 397 (FIG. 1). The ITS 1 region of *N. equi* was found to be 98% similar by Gap analysis to the ITS 1 sequence of *N. caninum* (SEQ ID NO:2).

The difference in the amplified ITS 1 region of NE 1 at nt 247 was confirmed by VspI restriction enzyme digestion and electrophoresis through an ethidium bromide stained gel. The VspI restriction enzyme recognized the dideoxynucleotide sequence, 5' AT/TAAT 3' which was present in the ITS 1 DNA sequences from *N. caninum* from nt 241 to nt 247 in the alignment analysis. However, *N. equi* was found to have the sequence, 5' ATTAAC 3', at nt 241 to nt 247 and was not cut the VspI restriction enzyme. The digestion was performed according to the standard protocol provided with the enzyme except, after 1 hour incubation, an additional 20 units of enzyme were added and after a second inoculation, the PCR products were incubated overnight to ensure complete digestion.

The level of sequence differences detected in the ITS 1 region of *N. equi*, as compared to *N. caninum* was greater than the ITS 1 sequence from 20 different *T. gondii* isolates. Therefore, we postulate that, based on ITS 1 sequences, the extent of divergence between *N. equi* and *N. caninum* is greater than that seen with different strains of *T. gondii*. This would support the placement of the NE 1 isolate into the genus Neospora but as a distinct species from *N. caninum*.

Thus far, the *N. caninum* isolates obtained from cattle and dogs from different continents can not be distinguished by molecular, antigenic or ultrastructural features. However, based on the ITS 1-rRNA gene regions, and the expression of antigenically distinct proteins, *N. equi* is closely related to *N. caninum*, but sufficient divergence has occurred to merit its classification as a distinct species.

Example 4

The DNA prepared in Example 3 are used to design primers and probes for the detection of Neospora in horses. This procedure is done as a diagnostic test to determine whether a horse exhibiting symptoms of equine protozoal myeloencephalitis (EPM) is infected with *Neospora equi*. For sample preparation, spinal fluid, other neurological tissue or a non-neurological tissue is used. To release the tachyzoite DNA, the sample is lysed prior to amplification of DNA. For the purposes of a necropsy, the tissue is preferably from the brain of an afflicted animal. The amplification protocol is as follows.

Oligonucleotide PCR primers

1) Equine Neospora Forward Primer 5' GGAAG-TAAAAGTCGTAACAAGG 3' (SEQ ID NO:3)

2) Equine Neospora Reverse Primer 5' GCTGCGTTCT-TCATCGATGC 3' (SEQ ID NO:4)

DNA amplification is typically carried out in a total volume of 50 μL. The sample mixture is made 10 mM Tris-HCl (pH 9.0), 50 mM potassium chloride, 0.1% Triton X-100, and 2.0 mM magnesium chloride. 200 mM of each deoxynucleoside triphosphate, 0.20 μM SEQ ID NO:3 and 0.20 μM SEQ ID NO:4 are added to the reaction mixture. After precycle denaturation at 94° C. for 4 min to reduce nonspecific amplification, 2.5 units of Taq DNA polymerase (Promega Corp., Madison, Wis.) is added and the mixture is overlaid with 50 μL of mineral oil or a wax bead. Amplification is preferably performed in a Robo Cycler (Stratagene Corp., San Diego, Calif.), however other thermal cyclers from other manufacturers are used. Amplification is allowed to proceed for 31 cycles as follows: an initial denaturation step for 2 minutes, denaturation at 94° C. for 1 min, 15 sec, annealing at 48° C. for 1 min, 15 sec, and extension at 72° C. for 2 min. The last cycle is typically given a prolonged extension period of 7 min. After amplification, 5 μL of each sample or a DNA molecular weight marker, such as BioMarker Low (BioVentures, Inc., Murfreeboro, Tenn.) DNA size standards, are mixed with 1 μL of 6X loading dye and electrophoresed on a 2% Nusieve® 3:1 agarose gel (FMC Bioproducts).

The gel is stained in a 0.5 μg/mL ethidium bromide solution for 30minutes and observed for the presence of amplification products under ultraviolet illumination. If Neospora spp. are present, amplification products will appear. If the EPM is caused by another agent, such as *Sarcocystis neurona*, no PCR products will appear or the bands in the electrophoretic gel will be of a different size than those expected from Neospora.

If it is necessary to determine whether the infectious agent is *N. equi* or *N. caninum*, a restriction digest, as in Example 3, are performed on the PCR products before electrophoresis.

Because a spinal fluid sample that is retrieved from a horse is quite large, in addition to a PCR based assay, a simple hybridization assay may be done. The spinal fluid or other neurological sample (such as brain from a horse to be necropsied) is lysed and the DNA isolated. DNA isolation are done by any method known in the art, see, Ausubel, supra.

Oligonucleotide DNA probes

3) NE 1/Neospora Primer Sequences 5' CTCCTTTG-GAGAGGGGTA 3' (SEQ ID NO:5) and 5' TCTTC-CATCAAACGCTATC 3' (SEQ ID NO:6)

4) Neospora Internal Probe Sequence
5'-AATTAACGTCT-3' (NE 1) (SEQ ID NO:7)
5'-AATTAATGTGT-3' (*N. caninum*) (SEQ ID NO:8)

Genomic DNA samples from neurological tissue are prepared as above. In a simple approach to hybridization, the genomic DNA is denatured (by incubating in NaOH or another technique well known in the art) and approximately 20–100 μL is applied to wells of a dot blot apparatus. Vacuum is applied to remove the liquid and concentrate the DNA on a spot on a membrane, preferably nylon. The DNA is then cross-linked to the membrane by exposure to UV light. The membrane with the DNA is hybridized to one of the oligonucleotide probes listed above. Preferably, the probe is labeled so that positive hybridization signals are visualized. After hybridization, the probe is removed and the membrane washed under stringent conditions to remove non-specifically bound probe. After drying, the membrane is handled in such a manner that hybridization signals are visualized.

In another type of hybridization assay, the genomic DNA is digested with restriction enzymes. Instead of applying them directly to a membrane, the fragments are first electrophoresed through an agarose gel. The DNA is transferred to a membrane by Southern blotting and probed as above. By this technique, it is possible to detect not only the presence of specific, identifiable, sequences of DNA, but also species and even allelic variants.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A biologically pure culture of equine Neospora having all the characteristics of ATCC Acession No. 209622 (NE1).

2. The culture of claim 1, which is of ATCC Accession No. 209622.

* * * * *